(12) United States Patent
Chisholm et al.

(10) Patent No.: US 11,370,865 B2
(45) Date of Patent: Jun. 28, 2022

(54) HARDENABLE MULTI-PART ACRYLIC COMPOSITION

(71) Applicant: Lucite International Speciality Polymers and Resins Limited, Billingham (GB)

(72) Inventors: Michael Stephen Chisholm, Newton Aycliffe (GB); Sera Saheb Abed-Ali, Newton Aycliffe (GB)

(73) Assignee: MITSUBISHI CHEMICAL UK LIMITED, Billingham (GB)

( * ) Notice: Subject to any disclaimer, the term of this patent is extended or adjusted under 35 U.S.C. 154(b) by 166 days.

(21) Appl. No.: 16/491,651

(22) PCT Filed: Mar. 15, 2018

(86) PCT No.: PCT/GB2018/050656
§ 371 (c)(1),
(2) Date: Sep. 6, 2019

(87) PCT Pub. No.: WO2018/167489
PCT Pub. Date: Sep. 20, 2018

(65) Prior Publication Data
US 2021/0079147 A1    Mar. 18, 2021

(30) Foreign Application Priority Data
Mar. 16, 2017    (GB) ..................................... 1704199

(51) Int. Cl.
| C08F 265/06 | (2006.01) |
| C08K 3/013 | (2018.01) |
| A61K 6/889 | (2020.01) |
| A61K 6/71 | (2020.01) |
| A61L 24/00 | (2006.01) |
| C08L 33/12 | (2006.01) |

(52) U.S. Cl.
CPC .............. *C08F 265/06* (2013.01); *A61K 6/71* (2020.01); *A61K 6/889* (2020.01); *A61L 24/001* (2013.01); *C08K 3/013* (2018.01); *C08L 33/12* (2013.01); *A61L 2430/02* (2013.01)

(58) Field of Classification Search
None
See application file for complete search history.

(56) References Cited

U.S. PATENT DOCUMENTS

| 4,184,992 A  * | 1/1980 | Hosaka ................. C08F 220/12 351/159.02 |
| 2008/0039586 A1* | 2/2008 | Hasenwinkel .......... A61L 24/06 525/192 |
| 2015/0051603 A1* | 2/2015 | Chisholm ............. C08F 265/06 606/94 |
| 2016/0243274 A1* | 8/2016 | Chisholm ............... A61L 27/16 |
| 2016/0279289 A1* | 9/2016 | Chisholm ............... A61L 27/50 |
| 2021/0079147 A1* | 3/2021 | Chisholm ............... A61P 31/10 |

FOREIGN PATENT DOCUMENTS

| WO | 2010018412 A1 | 2/2010 |
| WO | 2013144590 A1 | 10/2013 |
| WO | 2015044688 A1 | 4/2015 |
| WO | 2015044689 A1 | 4/2015 |

OTHER PUBLICATIONS

United Kingdom Search Report for Application No. GB1704199.7; dated Oct. 19, 2017; 5 pages [Applicant has cited only new art herewith; remaining art was cited in IDS filed Sep. 6, 2019].
V L Dimonie et al; "Emulsion Polymerization and Emulsion Polymers," P. A. Lovell and M. S. El-Aasser Eds John Wiley & Sons Ltd Chapter 9 pp. 294-326 (1997) (copy is not available).
International Preliminary Report on Patentability and Written Opinion of the International Searching Authority for International Application No. PCT/GB2018/050656; dated Sep. 17, 2019; 10 pages (References have been previously cited).
International Search Report and Written Opinion for application PCT/GB2018/050656; dated Sep. 12, 2018; 19 pages.

* cited by examiner

*Primary Examiner* — Peter A Salamon
(74) *Attorney, Agent, or Firm* — Shumaker, Loop & Kendrick, LLP

(57) ABSTRACT

A hardenable multi-part acrylic composition having at least two parts that react upon mixing to form a cement, such as bone cement, which hardens to a solid is described that includes storage stable liquid first and second parts, and optionally, further liquid parts. The parts react upon mixing to form a cement that hardens to a solid. The composition includes an acrylic monomer component and an initiator component in an amount effective to polymerize the acrylic monomer component when mixed and/or activated with it. The liquid first part comprises an aqueous dispersion of acrylic polymer particles and acrylic polymer beads. The polymer beads are at an equilibrium water content with the aqueous phase of the dispersion that generally has a viscosity between 10 and 10,000 centipoise. A twin barreled syringe, caulking gun or other cement mixing and delivery device and a method of producing the composition are also described.

46 Claims, No Drawings

HARDENABLE MULTI-PART ACRYLIC COMPOSITION

CROSS REFERENCE TO RELATED PATENT APPLICATIONS

This application claims the benefit of and priority to PCT/GB2018/050656 filed Mar. 15, 2018 which claims the benefit of and priority to Great Britain Application No. 1704199.7 filed on Mar. 16, 2017.

TECHNICAL FIELD AND BACKGROUND OF THE INVENTION

The present invention relates to a hardenable multi-part acrylic composition, in particular but not exclusively, a hardenable multi-part acrylic composition having at least two parts which react upon mixing to form a cement, such as a bone cement, which hardens to a solid. The present invention further relates to a twin barreled syringe, caulking gun or other cement mixing and delivery device accommodating the multi-part composition and a method of producing the hardenable multi-part acrylic composition.

WO2013/144590 discloses hardenable two part acrylic compositions for the treatment of human or animal bone. The composition comprises a liquid first part and a liquid second part which react with each other upon mixing to form a cement which hardens to a solid. The monomer component and the initiator component are generally located in separate parts of the two part composition so that the monomer component is storage stable. The liquid first part comprises emulsion polymerized acrylic polymer particles in a liquid carrier. In addition several examples with Colacryl® polymer beads added to the liquid first part are disclosed.

However, in such formulations viscosity increases over time with a corresponding shortening of shelf life for the liquid phase of the emulsion derived liquid first part of such compositions. A further problem of such formulations is the potential settling of any polymer beads if the water content of the formulation is too high. Increased water content results in a decrease in formulation viscosity, thus affecting the stability of the dispersion. Accordingly, addition of extraneous liquid to the formulation is generally sought to be minimised or even avoided. Accordingly, there continues to be a requirement for further improvements to such compositions.

Surprisingly, the present inventors have discovered that the shelf life of multi-part acrylic compositions comprising a monomer liquid component and a liquid component of acrylic polymer particles and acrylic polymer beads in a dispersion as set out above can be increased.

BRIEF SUMMARY OF THE INVENTION

According to a first aspect of the present invention there is provided a hardenable multi-part acrylic composition including a storage stable liquid first part, a storage stable liquid second part and optionally, a third or further liquid parts, which react upon mixing to form a cement which hardens to a solid, the composition comprising an acrylic monomer component, an initiator component in an amount effective to polymerize the acrylic monomer component upon being mixed and/or activated therewith, wherein the liquid first part comprises an aqueous dispersion of acrylic polymer particles and acrylic polymer beads suspended in the said aqueous dispersion characterized in that the polymer beads in the dispersion are at an equilibrium water content with the aqueous phase of the dispersion.

According to a further alternative aspect of the present invention there is provided a hardenable multi-part acrylic composition including a liquid first part, a liquid second part and optionally, a third or further liquid parts, which react upon mixing to form a cement which hardens to a solid, the composition comprising an acrylic monomer component, an initiator component in an amount effective to polymerize the acrylic monomer component upon being mixed and/or activated therewith, wherein the liquid first part comprises an aqueous dispersion of acrylic polymer particles and acrylic polymer beads suspended in the said aqueous dispersion characterised in that the liquid first part is storage stable.

As indicated, the composition may include more than two parts, for instance the initiator component could be stored in a separate third part. However, for convenience, the multi-part acrylic composition of any of the aspects of the invention herein is typically only a two-part composition i.e. there is typically no third or further part.

Preferably, the said monomer component and the said initiator component are located in separate parts of the said two part composition until ready for use, so that the monomer component is storage stable. Typically, the liquid second part comprises the acrylic monomer component.

Typically, the polymer beads are adapted so as to have a water absorption capacity when initially added to the dispersion that does not exceed that which would cause the dispersion to destabilise before or once the beads reach their equilibrium water content with the aqueous phase of the dispersion. In an embodiment of the present invention, the polymer beads may be adapted so as to be either fully or partly saturated with water, prior to addition to the composition, more preferably, to be at their equilibrium water content for the dispersion prior to addition thereto.

Therefore, according to a further aspect of the present invention there is provided a hardenable multi-part acrylic composition comprising a storage stable liquid first part, a storage stable liquid second part and optionally, a third or further liquid parts, which react upon mixing to form a cement which hardens to a solid, the composition further comprising an acrylic monomer component, an initiator component in an amount effective to polymerize the acrylic monomer component upon being mixed and/or activated therewith, wherein the liquid first part comprises acrylic polymer beads suspended in an aqueous dispersion of acrylic polymer particles characterized in that the polymer beads in the dispersion are at an equilibrium water content with the aqueous phase of the dispersion and in that the dispersion has a viscosity between 10 and 10,000 centipoise.

Thus, advantageously in the present invention when the polymer beads are at or near to their equilibrium water content prior to addition to the dispersion, destabilisation of the aqueous dispersion is prevented and the shelf life of the hardenable acrylic composition is increased.

Preferably, the equilibrium water content of the acrylic polymer beads when suspended in the aqueous dispersion is in the range 1.0-15% w/w, more preferably 1.2-13% w/w, most preferably 1.5-11% w/w with respect to the amount of acrylic polymer beads.

Preferably, the equilibrium water content of the acrylic polymer beads when suspended in the aqueous dispersion is less than 16% w/w, more preferably less than 14% w/w, most preferably less than 12% w/w w with respect to the amount of acrylic polymer beads.

Preferably, the equilibrium water content of the acrylic polymer beads when suspended in the aqueous dispersion is more than 0.7% w/w, more preferably more than 0.9% w/w, most preferably more than 1.2% w/w with respect to the amount of acrylic polymer beads.

Preferably, the equilibrium water content of the acrylic polymer beads when suspended in the aqueous dispersion is in the range 0.6-10% w/w, more preferably 0.7-8% w/w, most preferably 0.9-7% w/w with respect to the amount of liquid first part.

Preferably, the equilibrium water content of the acrylic polymer beads when suspended in the aqueous dispersion is less than 10% w/w, more preferably less than 8% w/w, most preferably less than 7% w/w w with respect to the amount of liquid first part.

Preferably, the equilibrium water content of the acrylic polymer beads when suspended in the aqueous dispersion is more than 0.4% w/w, more preferably more than 0.5% w/w, most preferably more than 0.7% w/w with respect to the amount of liquid first part.

Preferably, the equilibrium water content of the acrylic polymer beads when suspended in the aqueous dispersion is in the range 0.3-5% w/w, more preferably 0.4-4% w/w, most preferably 0.5-3.5% w/w with respect to the amount of hardenable composition.

Preferably, the equilibrium water content of the acrylic polymer beads when suspended in the aqueous dispersion is less than 5% w/w, more preferably less than 4% w/w, most preferably less than 3.5% w/w w with respect to the amount of hardenable composition.

Preferably, the equilibrium water content of the acrylic polymer beads when suspended in the aqueous dispersion is more than 0.2% w/w, more preferably more than 0.3% w/w, most preferably more than 0.4% w/w with respect to the amount of hardenable composition.

Typically, the equilibrium water content of the acrylic polymer beads is defined by the water saturation limit of the polymer beads in the aqueous dispersion.

Preferably, the water content provided by the continuous phase of the aqueous dispersion at equilibrium is in the range 8-30% w/w, more preferably 10-25% w/w, most preferably 12-20% w/w liquid first part.

Preferably, the water content provided by the continuous phase of the aqueous dispersion at equilibrium is greater than 8% w/w, more preferably 11% w/w, most preferably 13% w/w liquid first part.

Preferably, the water content provided by the continuous phase of the aqueous dispersion at equilibrium is less than 30% w/w, more preferably 27% w/w, most preferably 25% w/w liquid first part.

Preferably, the water content provided by the continuous phase of the aqueous dispersion at equilibrium is in the range 4-15% w/w, more preferably 5-12.5% w/w, most preferably 6-10% w/w hardenable acrylic composition.

When the acrylic polymer beads of the present invention are at their equilibrium water content, the tolerance of the dispersion is not exceeded and therefore the dispersion is stable.

Preferably, the acrylic polymer beads are present in the hardenable acrylic composition at an amount between 15-80% w/w, more preferably 20-70% w/w, most preferably 30-60% w/w.

The ratio of the acrylic polymer particles to the acrylic polymer beads in the hardenable acrylic composition varies depending on the final application. Preferably, the ratio of the acrylic polymer particles to the acrylic polymer beads is between 4:96 to 60:40 w/w thereof, more preferably 8:92 to 50:50, most preferably 10:90 to 40:60. Such ratios are advantageous in applications such as bone cements, providing a good balance between short dough times and long work times.

Preferably, the total water content of the liquid first part is in the range 16.0-40% w/w, more preferably 16.5-35% w/w, most preferably 17.0-25% w/w.

According to a second aspect of the present invention there is provided a method of producing a hardenable multi-part acrylic composition comprising a storage stable liquid first part, a storage stable liquid second part and optionally, a third or further liquid parts which react upon mixing to form a cement which hardens to a solid, comprising the steps of:

(a) emulsion polymerizing an acrylic monomer composition in the presence of excess initiator to produce an aqueous dispersion of acrylic polymer particles; or (b) emulsion polymerizing an acrylic monomer composition to produce an aqueous dispersion of acrylic polymer particles and adding initiator to the dispersion; or (c) emulsion polymerizing an acrylic monomer composition to produce an aqueous dispersion of acrylic polymer particles without excess initiator;

(d) mixing the dispersion from (a) or (b) or (c) with acrylic polymer beads, characterized in that the water absorption capacity of the polymer beads when mixed with the dispersion does not exceed the level that would cause the dispersion to destabilise.

By careful selection of the water absorbing capacity of the polymer beads at this level, it is possible for the polymer beads in the dispersion to reach or remain at their equilibrium water content without the dispersion destabilising or going below the tolerance level for the dispersion.

Preferably, the water absorption capacity of the acrylic polymer beads when suspended in the dispersion is in the range 0-20% w/w (of the dispersion), more preferably 0-15% w/w, most preferably 0-10% w/w.

Preferably, the water absorption capacity of the acrylic polymer beads when suspended in the dispersion is less than 10% w/w (of the dispersion), more preferably 5% w/w, most preferably 0% w/w.

Preferably, the water absorption capacity of the acrylic polymer beads when suspended in the dispersion is less than 5% w/w (of the beads), more preferably 3% w/w, most preferably 0% w/w.

Methods for preparing hardenable acrylic compositions comprising two liquid components known in the art typically involve drying the polymer beads prior to preparation of the composition. However, contrary to standard practises, it has been surprisingly found that adaption of the polymer beads in accordance with the invention can increase the shelf life of the acrylic composition, in particular, the liquid first part of the acrylic composition.

Typically, the polymer beads are adapted so as to have the water absorption capacity to enable the polymer beads to absorb water up to but not exceeding their water equilibrium level without the dispersion going below the tolerance level. In an embodiment of the present invention, the polymer beads may be adapted so as to be either full or partly saturated with water prior to addition to the dispersion.

DETAILED DESCRIPTION OF INVENTION

Acrylic Polymer Particles and Acrylic Polymer Beads

The aqueous dispersion of acrylic polymer particles forms an acrylic polymer dispersion as defined herein.

Typically therefore, the acrylic polymer dispersion (the aqueous dispersion of acrylic polymer particles) provides a continuous phase for the liquid first part. The acrylic polymer dispersion typically consists of the acrylic polymer particles, at least one emulsifier and water.

Typically, the acrylic polymer particles may include one or more sub-population(s) of acrylic polymer particles. The one or more sub-population(s) of acrylic polymer particle may be differentiated from each other by average particle size and/or molecular weight (Mw). For instance, there may be two, three or four sub-population(s) of acrylic polymer particle. References to sub-population herein include all populations when more than one population is present in the composition i.e the acrylic polymer particle or acrylic polymer bead of the invention may itself be described as a sub-population with respect to the other.

Preferably, the acrylic polymer particles herein are emulsion polymerized acrylic polymer particles. Preferably, the acrylic polymer particles are produced by conventional emulsion polymer processing. Preferably, the acrylic polymer particles are emulsion polymerized particles formed from emulsion polymerization, such that the emulsion particles may be coalesced together, agglomerated together or independent.

Mixing of the polymer beads with the aqueous dispersion forms a suspension of the acrylic polymer beads in the aqueous dispersion. Preferably, the acrylic polymer beads form a dispersion in the liquid carrier. Typically, this is a dispersion of the acrylic polymer beads in a continuous phase.

By the term "suspension" as used herein, is meant a non-solvated form and includes dispersions.

The method of manufacture of the acrylic polymer beads is generally conventional suspension or dispersion polymerization to produce generally spherical polymer beads. Alternatively, the acrylic polymer beads may be formed by other conventional polymerization techniques, followed by any necessary further treatment, such as milling, to produce conventional bead size polymer particles. Typically, the beads are made by suspension polymerisation.

Typically, the acrylic polymer beads may include one or more sub-population(s) of acrylic polymer bead. The one or more sub-population(s) of acrylic polymer bead may be differentiated from each other by average particle size and/or molecular weight (Mw). For instance, there may be two, three or four sub-population(s) of acrylic polymer bead.

Preferably, where there are three or more sub-population/s of acrylic polymer particles/beads there is at least 1 wt % of each sub-population, more preferably, 5 wt %, most preferably, 10 wt %.

The term "beads" or any variation thereof as used herein is not meant to be interpreted restrictively unless indicated otherwise and refers to a discrete polymer particle of any suitable size, shape and surface texture. (In the context of the present invention, the term "beads" may be used to differentiate the acrylic polymer beads from the acrylic polymer particles formed by emulsion polymerization.)

Typically, the acrylic polymer particles in the aqueous dispersion together with the acrylic polymer beads form at least 90% of the polymer present in the liquid first part of the multi-part acrylic composition prior to mixing of the liquid parts, more preferably, at least 95%, most preferably, approximately 100% of the polymer present in the liquid first part prior to mixing of the liquid parts. Upon mixing of the liquid parts, the monomer typically dissolves the initiator, acrylic polymer particles and/or acrylic polymer beads then polymerizes and causes the mixed composition to form a cement which gradually hardens, eventually setting to a solid. Typically, the solids content of the aqueous dispersion in the liquid first part of the multi-part acrylic composition is in the range 60-10% w/w, more typically 20-55% w/w, most typically, 30-52% w/w. The preferred ranges depend on the properties that are desired, e.g. mechanical properties. For example, to achieve a compressive strength in the resulting solid of greater than 40 MPa, the preferred range of solids content of the liquid first part of the multi-part acrylic composition is 70-90% w/w, more preferably 75-90% w/w, most preferably, 80-90% w/w.

The acrylic polymer particles and acrylic polymer beads typically form between 30-99.5% w/w of the solids content of the liquid first part of the multi-part acrylic composition, more preferably 35-99.5% w/w, most preferably 40-99.5% w/w. The balance is generally made up of other solids which may be fillers, pigments, dyestuffs, catalysts and initiator, although residual emulsifier may also be present.

The second part may include monomer, water or other solvent as the liquid component which is sufficient to provide a liquid carrier for the other components which may include other polymer composition components known to the skilled person such as polymer, initiator (if monomer is absent), fillers, pigments, dyestuffs, catalysts, accelerators, plasticisers etc. In this regard, although it is possible to use an initiator paste in a liquid carrier such as water or organic solvent, optionally in the presence of plasticizer to form the liquid second part, it is more typical to have acrylic monomer as the liquid carrier in the second part, optionally with acrylic polymer particles dissolved therein and with other components added such as accelerators, fillers, radiopacifiers, dyes etc. Generally, the amount of monomer in the unmixed composition, whether in the second part, or otherwise, is in the range 15-49.5% w/w, more preferably 17.5-40% w/w, most preferably 20-35% w/w.

The ratio of the liquid first part to the liquid second part is preferably in the range 1:5 to 5:1 by mass, more preferably 1:3 to 3:1 by mass.

When both monomer and polymer form the bulk of the liquid second part, the ratio of acrylic monomer:polymer is in the range 98:2 to 50:50, more preferably 95.5 to 60:40.

Preferably, the compressive strength of the solid produced by mixing the said first and second part in any aspect of the present invention is greater than 40 MPa, more preferably greater than 70 MPa. The typical range of compressive strengths found in the produced solid is 40-130 MPa, more preferably 70-130 MPa.

Preferably, the Z-average particle size of the acrylic polymer particles is less than 2000 nm as determined by light scattering using a Malvern Zetasizer nano series S particle size analyzer (adding one drop of dispersion to 1 ml of de-ionised water in a measurement cuvette, allowing the test sample to equilibrate at 25° C. and determining Z-average particle size using the software provided by the instrument), more preferably, less than 1000 nm, most preferably, less than 800 nm, especially, less than 500 nm. A preferred Z-average particle size range for the emulsion polymerized particles is between 10-2000 nm, more preferably, 20-1000 nm, most preferably, 50-500 nm, especially 100-450 nm, as determined by light scattering using a Malvern Zetasizer as above.

The weight average molecular weight (Mw) of the acrylic polymer particles is typically, between 25,000 daltons and 3,000,000 daltons, more typically, between 100,000 daltons and 1,500,000 daltons, preferably, between 250,000 and 1,000,000, for instance, between 250,000 and 600,000. Molecular weight may be determined for this purpose by gel permeation chromatography (GPC).

A core shell (C:S) ratio of the acrylic polymer particles is typically, between C:S 95:5% wt and C:S 40:60% wt, more typically, between C:S 90:10% wt and C:S 50:50% wt, preferably, between C:S 85:15% wt and C:S 70:30% wt.

Typically, the acrylic polymer particles may be single stage or multistage i.e. the so called core/shell particles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion particles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulphate) or through using emulsifiers. Once the seed particles are formed, the core and shell are formed from sequential addition of further aliquots of monomer and initiator.

The Brookfield viscosity range for the liquid first part and liquid second part may be between 10 and 10,000 centipoise, more preferably between 100 and 7,000 centipoise, still more preferably between 100 and 5,000 centipoise, most preferably between 200 and 4,000 centipoise. A free flowing liquid herein may be defined by such viscosity ranges.

Preferably, step (a) of the second aspect comprises seed, core and at least one shell emulsion polymerization step. A particularly preferred method introduces an excess of initiator into the emulsion polymerization step (a) so that residual initiator is encapsulated with the emulsion particles. Preferably, in a multistage emulsion polymerization, the excess initiator is introduced during the final stage so that it is present in the outer shell of the multistage particle. However, alternatively, initiator can also be added subsequently to the acrylic polymer dispersion.

An advantage of the emulsion polymerized acrylic polymer particles is the rapid dough time that is reached in the presence of the acrylic monomer composition. However, the working time and set time for the dough need to vary depending on the application. If a very short working time and set time are required then it is known that the emulsion polymerized acrylic polymer particles may be used alone. Nevertheless, in most applications, a longer working time and set time will be required and this can be achieved with addition of acrylic polymer bead and by varying the amount and particle size of the bead. Polymer particles/beads of smaller average particle size (e.g. typically <20 microns) are known to also give short working times but by increasing the amount of particles of larger particle size and by increasing the particle size itself, longer working times can be achieved. Accordingly, the particle size and amount of further acrylic polymer particles/beads depends upon the final application and this will be appreciated by the skilled person.

The polymer beads herein may contain encapsulated residual initiator as described for the emulsion polymerized acrylic polymer particles above.

Although the average particle size of the acrylic polymer beads herein is variable as mentioned above, depending upon the final application, a typical average particle size for the acrylic polymer beads herein is in the range 10-1000 microns (um), more typically, 20-600 microns, most typically, 25-300 microns. Where there is a sub-population of beads as well as a main population of beads, a smaller particle size sub-population may be in the range 10-100 microns and a larger particle size sub-population may be in the range 50-300 microns with the proviso that the larger particle size sub-population has a higher average particle size than the smaller average particle size sub-population.

Although, the molecular weights of the polymers in the polymer components of the hardenable composition may influence the dough and work times, the invention is not restricted to any particular molecular weight. In any case, reductions in the molecular weight and/or increases in the particle size of the further acrylic polymer particles can be used to increase the work time of the hardenable composition.

The weight average molecular weight (Mw) of the acrylic polymer beads, is typically, between 10,000 daltons and 3,000,000 daltons, more typically, between 30,000 daltons and 1,000,000 daltons, preferably, between 50,000 and 700,000, for instance, between 60,000 and 600,000 Daltons. Molecular weight may be determined for this purpose by gel permeation chromatography (GPC).

The larger the average particle size, the longer the working time. The skilled person will also appreciate that the molecular weight of the polymer and the presence of accelerators can also influence the working time and the set time. The invention is not restricted to a particular working time or set time because this will depend on the application.

There is no particular temperature limitation on the use of the present invention. Generally, however it is used at temperatures acceptable to the operator i.e. temperatures found during normal working conditions that may be encountered indoors or outdoors by the operator, for example 5-40° C. and atmospheric pressure and/or applied syringe pressure.

Notwithstanding the foregoing, a particularly advantageous application of the acrylic composition of the aspects of the invention is its use as bone cement compositions. Such compositions are used in vertebroplasty. A similar application for the compositions of the present invention is dental repairs.

Nevertheless, the advantages of the invention can be seen as generally desirable in many industrial applications and therefore, the invention is not restricted to bone cement and dental applications although these are preferred embodiments.

Emulsion polymerized particles are well known in the field of impact modifiers. For this reason an impact modifier such as butadiene or butyl acrylate is typically introduced as a comonomer into one of the shells of the multistage core shell particle. However, in the multi-part compositions of the present invention, an impact modifier may not be required. Accordingly, the emulsion polymerized acrylic polymer particles of the present invention may be free from impact modifier co-monomer residues.

Initiators and Further Components

The water carrier of the aqueous dispersion may include other components. These components may be dissolved in the water such as solubilizing agents selected from: polyethylene glycol, glycerol and D-sorbitol.

Typically, the level of filler in the multi-part acrylic composition is 0-49.9% w/w of the multi-part acrylic composition, more preferably, 2-39.9% w/w, most preferably, 5-34.9% w/w. The filler may be present in either one of the parts or may be distributed in multiple parts.

Accelerators may be present in the unmixed composition in the range 0.1 to 5% by mass, more typically, 0.5-3% by mass.

The total level of unreacted initiator, whether residual or added, in the multi-part acrylic composition is typically, 0.1-10% w/w of the multi-part acrylic composition, preferably, 0.15-5% w/w, more preferably, 0.2-4.0% w/w.

Where initiator is used in one of the components, this may be encapsulated within the polymer bead or polymer emulsion and/or separately added.

Where polymer is dissolved in monomer, the polymer must contain very low levels of residual initiator to avoid shortening of the shelf life.

The initiator may be present in both the acrylic polymer particles and the acrylic polymer beads that form the acrylic composition. The initiator in the acrylic polymer particles and acrylic polymer beads may be the residual amount of unreacted initiator used in the formation of the acrylic polymer particles and/or beads which is therefore the equivalent of the excess amount of initiator. Some initiator can alternatively or additionally be added as a separate component to the multi-part composition. In the acrylic polymer particles and/or beads, the level of residual initiator present before reaction with the second part is typically, 0.001-10% w/w of the acrylic polymer particles, preferably, 0.1-6% w/w, more preferably 0.1-5% w/w.

Preferably, the initiator is present at a level which will effect polymerization of the monomer component that is at least greater than 90% polymerization, more typically, greater than 93%, more typically greater than 95% polymerization.

Initiators that can be used to initiate the suspension polymerization of the acrylic polymer particles and therefore those which may form residual initiators in the composition to initiate the hardening process include: azo compounds, peroxides, peroxyesters and persulfates, specifically azobis (isobutyronitrile), azobis(2-methylbutyronitrile), azobis(2, 4-dimethylvaleronitrile), azobis(4-cyanovaleric acid), dilauroylo peroxide, tert-butyl peroxyneodecanoate, dibenzyl peroxide, cumyl peroxide, tert-butylperoxy-2-ethyl hexanoate, tert-butyl peroxydiethyl acetate, tert-butyl peroxy benzoate, tert-butyl hydroperoxide, potassium persulphate, ammonium persulphate and sodium persulpahte.

Initiators that can be used to initiate the emulsion polymerization of the acrylic polymer particles and therefore those which may form residual initiators in the composition to initiate the hardening process are persulphates, (e.g., potassium, sodium or ammonium), peroxides (e.g., hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

A particularly preferred initiator for the hardening stage is dibenzoyl peroxide.

Initiators that can be used for emulsifier free emulsion polymerization and therefore which may be present as residual initiators include: —ionic water-soluble initiators, such as potassium, sodium or ammonium persulphate.

In addition, any one or more of the above initiators can be added to the composition independently.

In a particularly preferred embodiment, the acrylic polymer particles incorporate the initiator in their polymer matrix. Accordingly, in this embodiment, the initiator is not added separately to the liquid first part of the composition.

Advantageously, the initiator for the multi-part acrylic composition according to the present invention can be added as excess initiator during the emulsion polymerization of the acrylic polymer particles so that some initiator is used in the polymerization of the emulsion particles but as the emulsion particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerization process and, accordingly, excess initiator is used in the final shell polymerization stage. During polymerization of acrylic polymer particles, more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

For the avoidance of doubt, by "excess initiator" is meant, the portion of initiator that is not required to complete polymerisation of the acrylic polymer particles and/or beads and is available for subsequent reaction after the polymerization of the acrylic polymer particles and/or beads is completed.

Preferably, the emulsion polymerized acrylic polymer particles of the liquid composition incorporate a suitable initiator compound in their polymer matrix, in the case of multistage emulsion particles, the initiator is incorporated in their outer shell in the final stage.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT)

in the acrylic monomer composition can also affect the set time. Increased accelerator concentration results in shortened set time.

In medical and some dental applications, the filler used is advantageously an x-ray opaque filler so that it can be observed during treatment or surgery by x-ray. Suitable fillers for this purpose include the radiopacifiers mentioned herein encapsulated/absorbed within the polymer particles or beads or free. In the production of dentures or in industrial applications, other fillers may also be used and these will be known to the skilled person in the art of such fields. Additionally, organic x-ray opaque monomers can be used instead of fillers. These can be copolymerized into any of the acrylic polymer particles or acrylic polymer beads during their production or incorporated into the acrylic monomer composition. Typical organic x-ray opaque monomers include halogenated methacrylates or acrylates, e.g., 2,3-dibromopropyl methacrylate or 2-methacryloyloxyethyl-2,3,5-triiodobenzoate.

Emulsifiers that can be used in the emulsion polymerization and therefore those which are present in the subsequent liquid first part are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxyethyl)-N-octadecyl sulfosuccinate, sodium salt of sulphated alkylphenol ethoxylates, sodium alkane sulfonate, sodium dodecyl sulphate or sodium 2-ethylhexyl sulphate), nonionic (e.g., polyethylene glycol nonylphenyl ethers, polyethylene oxide octylphenyl ethers, or di-functional ethylene oxide/propylene oxide block copolymers) or cationic emulsifiers (e.g., hexadecyltrimethylammonium bromide or alkyl polyglycoletherammonium methyl chloride). Reactive or polymerisable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethylhexadecyldimethylammonium bromide.

The mixing of the further components of the aqueous dispersion may be carried out by any suitable technique known to the skilled person for mixing solids or liquids with a liquid.

Radiopacifying Fillers

As mentioned above, fillers may include radiopacifying fillers.

Suitable radiopacifying fillers may be selected from the list comprising zirconium dioxide, strontium carbonate, powdered tantalum, powdered tungsten, barium sulphate and mixtures thereof. The radiopacifying filler may more suitably be barium sulphate or zirconium dioxide.

By radiopacifying herein is meant the ability to render a material more distinguishable from surrounding material when subjected to X-rays.

The radiopacifying filler may be added to any or both parts of the composition. It has been found advantageous however for at least some of the radiopacifying filler to be encapsulated within and/or adsorbed on the acrylic polymer particles/beads in a liquid part.

Notwithstanding the above, it is also possible for some or all of the radiopacifying filler to be present in the composition and/or hardened cement in a form that is not encapsulated and/or adsorbed in or on acrylic polymer particles/beads, for example in the liquid first part and/or liquid second part. This is either independently added radiopacifying filler or radiopacifying filler that has migrated from an encapsulated or adsorbed form into the surrounding liquid.

The radiopacifying filler may be encapsulated within and/or adsorbed on the acrylic polymer particles or the acrylic polymer beads.

In the present invention whether there are the two or more than two sub-populations of acrylic polymer particles or beads in the composition, any encapsulated and/or adsorbed radiopacifying filler may be encapsulated and/or adsorbed in only one sub-population or in more than one sub-population of acrylic polymer particles or beads. Preferably, however, the radiopacifying filler is encapsulated within and/or adsorbed on the polymer beads or in two or more bead sub-populations.

Typically, when the radiopacifying filler is barium sulphate, the barium sulphate is both encapsulated in and adsorbed on the acrylic polymer particles/beads, more typically, bead polymer particles. On the other hand, for other radiopacifying fillers such as zirconium dioxide, the zirconium dioxide is generally only encapsulated.

Typically, at least 25% w/w of the total radiopacifying filler present in the composition and therefore, typically, also in the final hardened composition, is encapsulated within and/or adsorbed on acrylic polymer particles and/or beads, more typically, at least 50% w/w, most typically, at least 75% w/w is so encapsulated and/or adsorbed.

Therefore, between 20 and 100% w/w of the radiopacifying filler in the composition and therefore, typically, also in the final hardened composition, is encapsulated within and/or adsorbed on acrylic polymer particles and/or beads, more typically, between 30% and 100% w/w, most typically, between 60 and 100% w/w. Although it is preferred for the level of encapsulated and/or adsorbed radiopacifying filler to be maintained in the final hardened composition there may nevertheless be some dissolution of the carrier particle in the monomer and accordingly, in the alternative, the level of the radiopacifying filler in the final hardened composition which is encapsulated within and/or adsorbed on acrylic polymer particles and/or beads is between 10 and 100% w/w, more typically, between 20% and 95% w/w, most typically, between 50 and 90% w/w.

Typically, the level of radiopacifying filler in the hardenable multi-part composition of the invention is between 1 and 50% w/w, more typically, between 5 and 40% w/w most typically, between 6.5 and 30% w/w. Preferably, the radiopacifying filler is present at the composition levels specified encapsulated within or adsorbed on the acrylic polymer particles and/or beads. Typically, the radiopacifying filler is present at or around the compositional levels specified encapsulated within or adsorbed on the acrylic polymer particles and/or beads in the hardened cement i.e. the fully polymerised product. Accordingly, the encapsulated and or adsorbed radiopacifying filler should preferably not be released into the matrix monomer and is therefore typically present at the composition levels specified in or on acrylic polymer particles and/or beads in suspension in a liquid part of the hardenable composition. However, during mixing some of the adsorbed radiopacifying filler may migrate into the monomer and, in addition, some of the polymer particle and/or bead may dissolve thus releasing radiopacifying filler into the matrix monomer. Accordingly, the level of encapsulated radiopacifying filler present in the final hardened cement may be reduced from the compositional levels above by up to 40%, more typically, by up to 20%.

Advantageously, a high level of encapsulation in the final hardened product is also achieved by incorporating one or more sub-population(s) of acrylic polymer particles and/or beads into the composition having a lower average particle size than the average particle size of the sub-population(s) having encapsulated and/or adsorbed radiopacifying filler. The average particle size of these lower average particle size acrylic polymer particles and/or beads is typically <30 µm, more typically <20 µm, most typically <10 µm. Typical lower average particle size sub-population ranges being 0.01-30 µm, more typically, 0.02-20 µm, most typically, 0.1-10 µm. Such lower average particle size sub-populations may be present in any of the liquid parts of the hardenable composition but are generally kept apart from the monomer so that they preferentially dissolve in the monomer after mixing thereby preventing or reducing dissolution of the sub-population(s) having encapsulated and/or adsorbed radiopacifying filler. Accordingly, the larger average particle size acrylic polymer particles and/or beads with encapsulated and/or adsorbed radiopacifying filler do not dissolve or do not dissolve to the same extent in the monomer as the lower average particle size sub-population(s).

Accordingly, when emulsion particles, the Z-average particle size of the lower average particle size sub-population(s) is preferably in the range 0.01 to 2 µm, more preferably, 0.02 to 1 µm, most preferably, 0.05 to 0.5 µm, especially, 0.1 to 0.45 µm.

When bead particles, the mean particle size of the lower average particle size sub-population(s) added to have improved dissolution in the monomer than a higher average particle size bead particle is preferably, in the range 1-30 µm, more preferably, 2-20 µm, most preferably, 2.5-15 µm.

Although any acrylic polymer particle may be used as the lower average particle size sub-population(s), it is preferred that emulsion particles as defined herein are used.

The average particle size of the sub-population(s) having encapsulated and/or adsorbed radiopacifying filler is preferably in the range 10 to 1000 µm, more preferably, 20 to 600 µm, most preferably, 25 to 200 µm. Generally, in such ranges this should be taken to refer to mean particle size.

Generally, herein the average particle size is determined by a technique appropriate to the size of the particle being characterised. Accordingly, a lower average particle size sub-population may have its average particle size characterised by a different technique than the sub-population it is being compared with. Nevertheless, this is appropriate where the average particle sizes of the relevant sub-populations are clearly distinguishable. Where the average particle size is relatively close it may be appropriate to use only the same technique. For instance, sub micron particles may be characterised by their Z-average particle size whereas particles>10 µm can be characterised by their mean particle size. Particles between 1 and 10 µm could be characterised by either measurement and if both sub-populations for comparison fall in this range then the same technique should be adopted. Accordingly, herein, emulsion particles are preferably characterised by their Z-average particle size and bead particles are preferably characterised by their mean particle size.

Preferably, the lower average particle size sub-population particle size is sufficiently lower than the sub-population having encapsulated and/or adsorbed radiopacifying filler particle size to retard dissolution of the latter in monomer. Preferably, the average particle size is at least 10% lower than the average particle size of the larger particle.

Preferably, where there are the two or more than two sub-populations, the radiopacifying filler is encapsulated and/or adsorbed in only one sub-population of acrylic polymer particles/beads but it may be encapsulated and/or adsorbed in more than one sub-population as mentioned above. Typically, the radiopacifying filler is only encapsulated within and/or adsorbed on acrylic polymer beads but it may alternatively only, or additionally, be encapsulated in and/or adsorbed on emulsion polymerized acrylic polymer particles and in either case in the first and/or second part. Typically, it is convenient to encapsulate and/or adsorb the radiopacifying filler in only one part of the composition, preferably, the first part thereof. If radiopacifying filler is encapsulated and/or adsorbed in only one sub-population type of acrylic polymer further sub-population types of acrylic polymer may still be present in the composition. For instance, if the radiopacifying filler is encapsulated and/or adsorbed in the emulsion polymerized acrylic polymer particles or acrylic polymer beads, both types of particles may still be present in the composition. In preferred embodiments, composition includes acrylic polymer beads in both the first and second parts and emulsion polymerized acrylic polymer particles in the liquid first part and radiopacifying filler may be encapsulated and/or adsorbed in any one or more sub-populations of acrylic polymer particles and/or beads. Preferably, however, the radiopacifying filler is only encapsulated and/or adsorbed in acrylic polymer beads, more preferably in acrylic polymer beads whether a sub-population or otherwise in the liquid first part.

Typically, at least 50% w/w of the total encapsulated and/or adsorbed radiopacifying filler in the composition is present in acrylic polymer beads, more typically, at least 90% w/w, most typically, at least 95% w/w is present in the acrylic polymer beads and more preferably at these levels in the acrylic polymer beads in the liquid first part. Especially preferred is for the filler to be present at these levels in such beads in suspension in the liquid part.

Encapsulation of the radiopacifying filler has the additional advantage of reducing the viscosity of the filled liquid part over the case where the radiopacifying filler is added as a separate component. For example, the viscosity may be reduced compared to a non-encapsulated radiopacifier equivalent system by 30% or more.

One method of encapsulation is to disperse the radiopacifying filler such as barium sulphate within acrylic monomer, then polymerize the monomer by, for example, bulk, emulsion or suspension polymerization, thereby encapsulating the radiopacifying filler within the resulting acrylic polymer particles/beads. The preferred approach is to encapsulate the radiopacifying filler within bead polymer particles such as those produced by suspension polymerisation.

It has been surprisingly found that by encapsulating the radiopacifying filler within acrylic polymer particles/beads, the concentration of radiopacifying filler particles in the continuous matrix formed by mixing the liquid first part and liquid second part is reduced, thereby reducing the number of stress concentrating defects in the continuous matrix. As a result, the normal reduction in mechanical properties that would occur if all the filler was to be found in the continuous matrix can be avoided. Further, by initially finely dispersing the radiopacifying filler in monomer and then encapsulating it within the acrylic polymer, it is possible to achieve the same radiopacifying effect through use of an even lower amount of filler. This leads to a further enhancement in mechanical properties. In addition, the viscosity of the liquid part is reduced thus facilitating better viscosity matching between the respective liquid parts, particularly if the radiopacifier is found in the liquid first part and the monomer component is found in the liquid second part.

In particularly preferred aspects of the present invention, the liquid part containing the acrylic polymer beads and encapsulated and/or adsorbed radiopacifying filler further contains the emulsion polymerized acrylic polymer particles.

Typically, therefore, the acrylic polymer dispersion provides a continuous phase for the liquid first part. Typically, the acrylic polymer dispersion herein comprises or consists of emulsion polymerized acrylic polymer particles, at least one emulsifier and water. However, the aqueous dispersion of the present invention also has acrylic polymer beads suspended therein. Accordingly, properties (such as viscosity) of the aqueous dispersion herein are properties with the acrylic polymer beads suspended therein unless indicated otherwise. Furthermore, when the aqueous dispersion forms the liquid first part herein then properties of the liquid first part are properties of the aqueous dispersion and vice versa unless indicated otherwise.

As indicated, the composition may include encapsulated and/or adsorbed radiopacifier. These particles or beads may be made in accordance with techniques known to those skilled in the art. However, preferred features of production include: emulsion polymerizing at least one acrylic monomer composition in the presence of radiopacifying filler to produce an acrylic polymer dispersion with encapsulated and/or adsorbed radiopacifying filler; and/or suspension, bulk or solution polymerizing at least one acrylic monomer composition in the presence of radiopacifying filler to produce an acrylic polymer bead particle with encapsulated and/or adsorbed radiopacifying filler.

Preferably, at least 90% w/w of the total radiopacifying filler in the composition is present in one part of the liquid composition, more preferably, at least 95% w/w, most preferably, at least 99% w/w and in any case, preferably in suspension therein. In preferred embodiments, substantially all the radiopacifying filler in the composition is present in one part of the liquid composition, preferably in suspension therein. Typically, therefore, the radiopacifying filler is present in only one part of the composition which may be the first or second part, more typically, the first part. Notwithstanding, the above, the radiopacifying filler may be present in more than one part of the composition.

Preferably, at least 90% w/w of the total acrylic polymer particles/beads with encapsulated and/or adsorbed radiopacifying filler in the composition are present in the liquid first part, more preferably, at least 95% w/w, most preferably, at least 99% w/w and in any case, preferably in suspension therein. In preferred embodiments, substantially all the acrylic polymer particles and/or beads with encapsulated and/or adsorbed radiopacifying filler in the composition is present in the liquid first part, preferably in suspension therein. Typically, therefore, the acrylic polymer particles/beads with encapsulated and/or adsorbed radiopacifying filler are present in only one part of the composition prior to mixing.

Typically, all or substantially all of the said acrylic monomer component and the said acrylic polymer particles and/or beads with encapsulated and/or adsorbed radiopacifying filler are located in separate parts of the said composition so that encapsulated and or adsorbed radiopacifying filler is not released into the monomer component prior to mixing and therefore released radiopacifying filler presence in the polymer matrix of the final hardened material is reduced.

Further Aspects

The acrylic composition first part of the present invention may be provided separately as a liquid either with or without added further components as defined herein for later use as a liquid first part in a hardenable composition.

Accordingly, the invention extends to a storage stable liquid first part for a hardenable multi-part acrylic composition according to any aspect of the present invention comprising an aqueous dispersion of acrylic polymer particles and acrylic polymer beads suspended in the said aqueous dispersion characterized in that the polymer beads in the dispersion are at an equilibrium water content with the aqueous phase of the dispersion.

In a preferred embodiment of any aspect of the invention, the liquid first part comprises emulsion polymerized acrylic polymer particles in a liquid carrier (preferably, PMMA dispersion), acrylic polymer beads in accordance with the first aspect of the present invention and initiator and the second part comprises acrylic monomer (preferably, MMA) and accelerator.

In a further preferred embodiment of the invention, the first part comprises emulsion polymerized acrylic polymer particles in a liquid carrier (preferably, PMMA dispersion), acrylic polymer beads in accordance with the first aspect of the present invention and initiator and the second part comprises a solution of initiator-free acrylic polymer (preferably, PMMA) in acrylic monomer (preferably, MMA) with accelerator.

Typically, in addition, in these preferred embodiments, radiopacifier may be present in either part.

In a preferred two-part embodiment of the invention the first liquid part comprises emulsion polymerized acrylic polymer particles in, preferably suspended in, a liquid carrier (preferably, PMMA dispersion), the acrylic polymer bead particle optionally with encapsulated and/or adsorbed radiopacifying filler (preferably PMMA bead) and initiator and the second part comprises acrylic monomer (preferably MMA monomer) and accelerator. Optionally, in this embodiment the Z-average particle size of the emulsion polymerized acrylic polymer particles is lower than the acrylic polymer bead mean particle size with encapsulated and/or adsorbed radiopacifying filler.

In a further preferred two-part embodiment of the invention the first part comprises emulsion polymerized acrylic polymer particles in, preferably suspended in, a liquid carrier (preferably PMMA dispersion), the acrylic polymer bead particle optionally has encapsulated and/or adsorbed radiopacifying filler and initiator and the second part comprises a solution of initiator-free acrylic polymer (preferably PMMA), in acrylic monomer (preferably MMA) with accelerator. Optionally, in this embodiment the Z-average particle size of the emulsion polymerized acrylic polymer particles is lower than the acrylic polymer bead mean particle size with encapsulated and/or adsorbed radiopacifying filler.

In a further preferred embodiment of the invention the first part comprises initiator-free acrylic polymer bead optionally with encapsulated and/or adsorbed radiopacifying filler (preferably PMMA bead), emulsion polymerized acrylic polymer particles in, preferably suspended in a liquid carrier, acrylic monomer (preferably, MMA monomer) and accelerator and the second part comprises an initiator paste. Initiator pastes are available commercially usually as a mixture with water or plasticiser. Optionally, in this embodiment the Z-average particle size of the emulsion polymerized acrylic polymer particles is lower than the mean particle size of the acrylic polymer bead particle with encapsulated and/or adsorbed radiopacifying filler.

According to a further aspect of the present invention there is provided a solid cement composition produced from mixing a multi-part acrylic composition according to any aspect of the present invention.

According to a further aspect of the present invention there is provided a process of producing an acrylic cement from a multi-part acrylic composition according to any aspect of the present invention comprising the step of mixing a first and second part.

The above process may be a manual mixing process. In addition, use of a manual mixing device such as an adapted syringe or caulking gun is envisaged. Furthermore, an automated mixing device may be used. Such devices, adapted for mixing of separate components and delivery of the mixed cement prior to hardening, are known to the skilled person in the art.

Therefore, according to a further aspect of the present invention there is provided a syringe or caulking gun or automated mixing device having at least two compartments comprising the liquid first part according to any aspect of the present invention in a first compartment thereof and a liquid second part according to any aspect of the present invention in the second compartment thereof and also comprising the further components of any aspects as disclosed herein.

The invention extends to a multi-part bone cement or dental cement or building cement or structural adhesive or laminating adhesive or jointing or sealing composition according to any aspects of the present invention.

Preferably, in a bone cement or dental cement composition the components thereof are biocompatible components at least once the composition is set to a solid.

For medical applications such as bone cement and dentistry to which the compositions of the invention are mainly directed the composition is biocompatible and in particular hardens to a solid cement or adhesive that is biocompatible in situ. Accordingly, the composition of the invention finds particularly advantageous utility as a medical implant material such as a bone cement or a solid effective in dental applications. Accordingly, the multi-part composition is typically a bone cement composition or dental composition.

According to a further aspect of the present invention there is provided a medical implant material produced from mixing a multi-part acrylic composition according to the present invention.

According to a still further aspect of the present invention there is provided a multi-part composition according to any aspects of the present invention for use in surgery, more particularly for use in the treatment of human or animal bone or teeth.

According to a still further aspect of the present invention there is provided a multi-part composition according to any aspect of the present invention for use in the replacement or partial replacement of human or animal bone.

According to a still further aspect of the present invention there is provided a multi-part composition according to any aspect of the present invention for use in dentistry, more particularly in the treatment of human teeth or animal teeth or for use in veterinary surgery, more particularly, for use in the treatment of hoof, nail or horn.

According to a still further aspect of the present invention there is provided a multi-part composition according to any aspect of the present invention for use in the replacement or partial replacement of human teeth or animal teeth, hoof, nail or horn.

In one preferred embodiment, the acrylic polymer composition liquid part containing the acrylic polymer particles and beads comprises a dispersion of polymerized acrylic polymer particles and only a single population of acrylic polymer bead particle, the former generally to control the dough time and the latter to generally control the working time.

The multi-part hardenable compositions of the invention also attain a low maximum exotherm temperature during hardening thus avoiding in the case of bone cements, tissue necrosis, a well known problem of acrylic bone cements.

The hardenable compositions formed from the invention also display a long working time thereby providing a longer time period for the operator to manipulate the cement dough in the desired fashion during application.

Advantageously, as water is the liquid carrier for the acrylic polymer particles/beads, the final cured hardened cement composition is porous. This porosity allows the mechanical properties of the hardenable composition to be matched to those of e.g. vertebral bone, thereby avoiding well known problems associated through implantation of artificial materials that are higher in modulus than the surrounding natural bone. However, the formulation can be also altered to adjust the level of porosity and vary the mechanical properties, e.g., to achieve mechanical properties that satisfy the requirements of ISO 5833:2002.

In addition, as a result of the porosity, the polymerization shrinkage upon setting of compositions of the invention may be lower than would normally be expected of conventional hardenable compositions based on powder/liquid combinations.

A still further advantage of the invention when used as a bone cement is that the control of porosity (size and topography) allows improved control over the controlled release of therapeutic agents such as antibiotics or antifungals into the surrounding bone and tissue.

According to a further aspect of the present invention there is provided a solid cement composition produced from mixing a multi-part acrylic composition according to the any aspect of the present invention which is porous. Typically, the solid cement porosity is adapted for controlled release of one or more therapeutic agents.

Accordingly, the invention extends to a multi-part composition or a liquid first part according to any aspect of the present invention comprising a pharmaceutically effective amount of a therapeutic agent. After mixing the multi-part acrylic composition, implanting and then forming the solid cement composition, the therapeutic agent elutes into the surroundings of the implant to provide a therapeutic, typically, an antimicrobial or antifungal effect.

Suitable therapeutic agents may be selected from the list comprising gentamicin, vancomycin, cefazolin, ciprofloxacin, linezolid, levofloxacin, rifampin, clindamycin and tobramycin. Such therapeutic agents may be used on their own or as mixtures of two or more therapeutic agents. The total amount of therapeutic agent to use is typically 1 to 5 wt % of the total liquid first part.

Definitions

By the term "aqueous dispersion of acrylic polymer particles" as used herein is meant a stable dispersion of acrylic polymer particles in water, in particular, a dispersion produced as a result of emulsion polymerisation including mini-emulsion polymerisation or high shear mixing of acrylic polymer powder in water to form a colloid of microscopically dispersed acrylic polymer particles suspended in a continuous phase of water.

By the term "equilibrium water content with the aqueous phase of the dispersion" as used herein is meant a water content of the acrylic polymer beads in the dispersion which is not subject to significant net changes under constant conditions of temperature and pressure. Advantageously, with the beads at their equilibrium water content there is no significant net change in the water content of the continuous phase of the aqueous dispersion, notwithstanding that the water content of the aqueous dispersion and acrylic polymer beads are in dynamic equilibrium, thus providing a storage stable liquid part, more particularly, a storage stable dispersion.

By "significant" net change is meant that insignificant changes are excluded. Such insignificant changes include small changes due to the ageing of the dispersion for instance by slow leaching of residual monomer out of the bead which will result in a slow change in the equilibrium water content. Generally, a "significant" change in water content is at least 0.2% w/w bead, more typically, at least, 0.5% w/w bead, most typically, at least 1.0% w/w bead.

By the term "water absorption capacity" as used herein is meant the capacity of the polymer beads to absorb water. The water absorption capacity of the polymer beads may not exceed the level that would cause the dispersion to destabilise. The water absorption capacity of the polymer beads is measured in terms of the increase in water content of the polymer beads from the time of mixing with the dispersion to reaching the equilibrium water content of the polymer beads.

By the term "destabilise" or variations thereof as used herein is meant the flocculation or solidification of the aqueous dispersion of acrylic polymer particles. Solidification or flocculation occurs when the water content of the aqueous dispersion goes below the tolerance level for the dispersion.

By the term "tolerance" as used herein is meant the minimum water content in the aqueous dispersion at which the dispersion remains storage stable.

By "located in separate parts" is meant that if one component is in first part then the further component is in a second or further part, for example, if the said monomer component is located in the second part then the said initiator component is located in the first part or further part.

The term "liquid" herein does not require definition because it is well understood by the skilled person. However, for the avoidance of doubt it includes a flowable material such as a slurry or paste that is thus susceptible of delivery through a syringe or caulking gun outlet by the application of pressure. Typically, the term liquid applies at least between 5 and 35° C., more typically, between 5 and 30° C.

By "storage stable" is meant that the monomer or liquid does not polymerize under normally acceptable storage conditions of temperature and time i.e. between 5 and 30° C. and 1 to 250 days, more typically, 15 to 25° C. and 1 to 170 days. In addition, by "storage stable" is meant in a liquid first part that it is and remains as a free flowing liquid, for example one having a viscosity between 10 and 10,000 centipoise such as between 100 and 7000, especially 200 and 4000, typically for a period of at least 6 months from initial bead/dispersion mixing, more typically, at least 12 months, most typically, 24 months. Accordingly, when the first liquid part is the aqueous dispersion with polymer beads suspended therein and the beads have reached an equilibrium water content with the aqueous phase of the dispersion then the dispersion is and remains as such, typically, for the above periods, a free flowing liquid until mixed and/or activated with a further liquid part as set out herein.

The term "population" is generally understood by the skilled person but for the avoidance of doubt refers to a plurality of polymer particles having a specific mean particle size, weight average molecular weight, particle size distribution and molecular weight distribution as is usually produced by monomer(s) which have undergone the same polymerization process(es) together and sub-population should be understood accordingly. The weight average molecular weight and particle size of such sub-populations may be in the ranges defined for the acrylic polymer particles and acrylic polymer bead herein.

By "acrylic polymer" as used herein, whether in relation to the acrylic polymer particles or acrylic polymer beads is meant independently for each type or sub-population a homopolymer of a polyalkyl(alk)acrylate or (alk)acrylic acid or copolymers of an alkyl(alk)acrylate or (alk)acrylic acid with one or more other vinyl monomers. Typically, a homopolymer of methyl methacrylate or a copolymer of methyl methacrylate with one or more other vinyl monomers is used. By other vinyl monomers is meant a further alkyl (alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid, acrylic acid; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers.

Copolymers containing functionalized monomers are of special interest because they may help in dispersing the X-ray radiopacifying fillers used in bone cement compositions (e.g. barium sulphate, zirconium dioxide, etc) into the liquid second part. Suitable functionalized monomers are well known in the field of pigment dispersion in inks and coatings. For example, amines such as N,N-dimethylaminoethyl methacrylate, N,N-diethylaminoethyl methacrylate, t-butylaminoethyl methacrylate and acids such as methacrylic acid and acrylic acid.

Crosslinking monomers can be used to crosslink one or more of the acrylic polymer particle sub-populations and/or acrylic polymer bead sub populations. For the emulsion polymerized particles, crosslinking may be carried out in the core and the shell, or only the core, or only the shell. Crosslinking serves the purpose of fine tuning the properties of the hardenable multi part acrylic composition.

By "acrylic monomer" as used herein is meant any suitable alkyl(alk)acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone, vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate and 1,6-hexanediol diacrylate, particularly the compatible acrylic crosslinking monomers. Typically, methyl methacrylate is used in the present invention.

The acrylic monomer of the invention is optionally, provided with an accompanying suitable inhibitor such as hydroquinone (HQ), methyl hydroquinone (MeHQ), 2,6-di-tertiary-butyl-4-methoxyphenol (Topanol 0) and 2,4-dimethyl-6-tertiary-butyl phenol (Topanol A). The inhibitor is present to prevent the monomer from spontaneously polymerising. A suitable inhibitor is 60 ppm of hydroquinone to ensure long shelf life at room temperature.

Polymerization activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for industrial applications the use of heat in "heat-cure" systems is also possible. For instance, dentures can be activated by heat.

Preferably, at least 90% w/w of the total acrylic monomer component in the composition is present in the liquid second part, more preferably, at least 95% w/w, most preferably, at least 99% w/w. In preferred embodiments, substantially all the acrylic monomer component in the composition is present in the liquid second part. Typically, therefore, the acrylic monomer component is present in only one part of the composition. Typically, the acrylic monomer component containing liquid part includes acrylic polymer dissolved therein.

By the term "alkyl" as used herein is meant $C_1$-$C_{18}$ alkyl wherein the terms "alkyl" and "alk" encompass cyclooalkyl and hydroxyl functional $C_1$-$C_{18}$ alkyl. By "alk" herein is meant $C_0$-$C_8$ alk wherein $C_0$ means no substituent for the hydrogen.

By "acrylic composition" is meant a composition where at least 50% of the total monomer and monomer residues present are present as or derived from one or more of the above defined acrylic monomers, more typically, is meant at least 70%, most typically, at least 95% or especially, at least 99% of the total.

The term "adsorbed" takes its usual meaning and means bound to the surface thereof.

The term "lower" herein in the context of average particle size or the like means having a lower value but is preferably, at least 10% lower than the comparative larger value, more preferably, at least 20% lower, most preferably at least 50% lower than the larger value.

The term "multi-part" herein means two or more parts, preferably two-part.

The Z-average particle size herein is determined by light scattering using a Malvern Zetasizer nano series S particle size analyzer.

The mean particle size herein may be determined using a Coulter LS230 laser diffraction instrument.

Preferably, at least 90% w/w of the total emulsion polymerized acrylic polymer particles present in the composition is present in the liquid first part, more preferably, at least 95% w/w, most preferably, at least 99% w/w. In preferred embodiments, substantially all the emulsion polymerized acrylic polymer particles in the composition is present in the liquid first part. Typically, therefore, the emulsion polymerized acrylic polymer particles are present in only one part of the composition.

Acrylic polymer bead may be present in any part of the composition, typically however, at least 70 wt % of the total acrylic polymer bead is present in the liquid first part, more typically, at least 80 wt %, most typically, at least 90 wt %, especially, 100 wt %. For these purposes, dissolved bead in monomer is no longer polymer bead.

Typically, all or substantially all of the said acrylic monomer component and the said emulsion polymerized acrylic polymer particles, if the latter is present, are located in separate parts of the said composition so that, for example, the liquid carrier of the first part is provided by the dispersion liquid carrier and a liquid carrier for the second part is provided by the acrylic monomer.

A general procedure for mixing the parts of the hardenable composition of the invention is described as follows: Before mixing, the two components are equilibrated for a suitable period, typically, 1 hour or more at a temperature of 5-40° C., more typically, 10-35° C., most typically, 15-30° C. The liquid first part is mixed with a suitable amount of liquid second part and, if present, any other liquid parts according to the ratios defined herein. Mixing is then carried out at the equilibrated temperature for at least 5, more typically, at least 20, most typically, at least 30 seconds. When the dough time has been reached, the doughed material is packed into place such as moulds preconditioned at an appropriate temperature generally in the range of the equilibration temperatures above and allowed to exotherm and harden. Alternatively, the doughed material may be implanted within some other cavity, such as bone and allowed to exotherm and harden.

The mixing of the two components and subsequent reaction can be carried out at the equilibration temperatures. The skilled person will be aware of the effect of temperature on the dough and set times. Higher mixing temperature leads to shorter dough and set times and vice versa for lower mixing temperature Embodiments of the invention will now be described with reference to the accompanying examples:

EXAMPLES

Characterisation Techniques:

The molecular weight was measured by gel permeation chromatography using poly(methyl methacrylate) standards for calibration. Tetrahydrofuran was used as the mobile phase. The weight average molecular weight (Mw), number average molecular weight (Mn) and the polydispersity (Mw/Mn) were measured.

The Z average emulsion particle size was determined using a Malvern Zetasizer nano series S particle size analyser.

The mean particle size of acrylic polymer beads was determined using a Coulter LS230 laser diffraction instrument.

Reduced viscosity (RV, dl/g) was measured in chloroform (1 wt % solution) using an Ubbelohde viscometer type OB at 25° C.

Wt % residual dibenzoyl peroxide content was determined by a titration method.

Wt % water content was determined by a Karl Fischer method using a Metrohm 874 over sample processor with 831 coulometer.

Brookfield viscosity (BV, centipoise (cPs)) of the liquid first part was determined using a Brookfield viscometer model DV-E at 25° C. operating with spindle number 6 and speed 50 rpm. The BV of the acrylic dispersions was determined using the same conditions except spindle number 5 and speed 20 was used.

Example 1

Preparation of 50.1% Wt Solids Acrylic Polymer Dispersion 600 grams of deionised water is added to a five-litre round bottomed glass flask fitted with a nitrogen inlet, condenser and electrically operated stainless steel paddle stirrer. The water is heated to 80° C. by means of a water bath whilst stirring at 150 revolutions per minute (rpm). A flow of nitrogen was passed through the vapour space of the flask above the surface of the liquid.

An emulsified monomer mixture was prepared consisting of 850 grams methyl methacrylate (MMA), 150 grams styrene, 5.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) was prepared by adding 30 grams of the emulsified monomer mixture to the flask followed by 10 millilitres of a 2 wt % solution of potassium persulphate in deionised water. Following a slight exotherm, the reaction proceeded for thirty minutes until the temperature returned to 80° C.

The core was then grown over the polymer seed particles (Stage 2) by firstly adding 10 millilitres of a 2 wt % solution of potassium persulphate in deionised water to the flask followed by continuous addition of 300 grams of the emulsified monomer mixture over approximately 25 minutes using a peristaltic pump. The reaction proceeded for a further 15 minutes after the completion of addition of the monomer mixture until the temperature returned to 80° C. This step was then repeated twice.

30.0 grams of 75% active dibenzoyl peroxide were dissolved in the remaining 370 grams of emulsified monomer mixture with stirring for 45 minutes.

The BPO-containing shell was then grown over the core (Stage 3) by firstly adding 10 millilitres of a 2 wt % solution of potassium persulphate in deionised water to the flask followed by continuous addition of the emulsified monomer mixture containing added BPO over approximately 25 minutes using a peristaltic pump. The reaction proceeded for a further fifteen minutes after all the monomer mixture had been added until the temperature had returned to 80° C.

The resultant acrylic polymer dispersion was then cooled to below 40° C. and filtered through a 150 micron screen.

The acrylic polymer dispersion had a solids content of 50.1% wt, reduced viscosity of 2.72 dl/g, Brookfield viscosity of 130 cPs, residual dibenzoyl peroxide of 1.8% wt and a z-average emulsion particle size of 245 nm.

Example 2

Preparation of Acrylic Polymer Beads

The aqueous phase of a suspension polymerization was prepared by adding 2000 millilitres of deionized water and 8 grams of hydroxyethyl cellulose powder (Natrosol HEC 250HR from Aqualon Ltd) to a 5 litre glass flask containing a stainless steel anchor-type stirrer. The flask contents were stirred at 400 rpm and heated to 40° C. to dissolve the hydroxyethyl cellulose. The organic phase containing 875 grams methyl methacrylate, 125 grams of styrene and 20.0 grams of 75% active dibenzoyl peroxide was then added, the stirrer speed adjusted according to the desired particle size of the resultant acrylic polymer beads and the contents of the reactor flask heated to 85° C. using a water bath. The polymerization was continued at 85° C. until the reactor contents experienced an exotherm, typically to approximately 94-96° C. The reactor flask was then cooled and the resultant acrylic polymer bead slurry was screened through a 850 micron sieve. The beads were then filtered, washed with deionized water and dried in an air circulating oven at 50° C. for varying times to produce acrylic polymer bead samples varying in water content. Two series of acrylic polymer bead samples were produced, i.e., polymer beads 1 and 2.

Polymer beads 1: The stirrer speed used during the polymerization was 650 rpm and the resultant product had mean particle size 34 μm, residual benzoyl peroxide content 1.3 wt %, weight average molecular weight (Mw) of 320,000 daltons and reduced viscosity 1.45 dl/g. Samples varying in water content from 0.5 to 31.8 wt % were produced, coded polymer beads 1(a) to 1(g).

Polymer beads 2: The stirrer speed used during the polymerization was 400 rpm and the resultant product had mean particle size 260 μm, residual benzoyl peroxide content 1.2 wt %, weight average molecular weight (Mw) 365,000 daltons and reduced viscosity 1.55 dl/g. Samples varying in water content from 0.5 to 13.0 wt % were produced, coded polymer beads 2(a) to 2(e).

TABLE 1

| | Drying time at 50° C. (hours:minutes) | Water content (% wt) |
|---|---|---|
| Polymer beads 1(a) | 10:00 | 0.5 |
| Polymer beads 1(b) | 6:00 | 2.8 |
| Polymer beads 1(c) | 5:40 | 3.1 |
| Polymer beads 1(d) | 3:30 | 8.4 |
| Polymer beads 1(e) | 2:00 | 12.0 |
| Polymer beads 1(f) | 1:00 | 17.2 |
| Polymer beads 1 (g) | 0:00 | 31.8 |
| Polymer beads 2(a) | 10:00 | 0.5 |
| Polymer beads 2(b) | 6:00 | 3.0 |
| Polymer beads 2 (c) | 5:30 | 3.75 |
| Polymer beads 2 (d) | 2:30 | 10.8 |
| Polymer beads 2(e) | 2:00 | 13.0 |

Examples 3-6

Preparation of Liquid First Part

The preparation of the liquid first parts was carried out by mixing the acrylic polymer dispersion prepared in example 1 with one each of a polymer bead 1 and 2 sample prepared in example 2. The general preparation method to make 300 grams of a liquid first part was as follows:

To a 500 ml polypropylene beaker equipped with electric stirrer motor and stainless steel paddle stirrer was added 90 grams of acrylic polymer dispersion. Stirring was commenced at 50 rpm. 63 grams of a polymer bead 1 (selected from samples 1(b) to 1(g)) was added and stirring maintained for a further 30 seconds. 73.5 grams of a polymer bead 2 (selected from samples 2(b) to 2(e)) was then added and stirring was continued for 30 seconds before adding the remaining amount (73.5 grams) of the polymer bead 2. Stirring was then continued for a further 60 seconds.

Comparative Example 1

Preparation of Liquid First Part

The preparation of the liquid first part was carried out by mixing the acrylic polymer dispersion prepared in example 1 with one each of a polymer bead 1 and 2 sample prepared in example 2. The general preparation method to make 300 grams of a liquid first part was as follows:

To a 500 ml polypropylene beaker equipped with electric stirrer motor and stainless steel paddle stirrer was added 60 grams of acrylic polymer dispersion. Stirring was commenced at 50 rpm. 72 grams of a polymer bead 1(a) was added and stirring maintained for a further 30 seconds. 84 grams of a polymer bead 2(a) was then added and stirring was continued for 30 seconds before adding the remaining amount (84 grams) of the polymer bead 2(a). Stirring was then continued for a further 60 seconds.

The identity of the polymer beads used in each of the liquid first parts of Examples 3 to 6 and Comparative Example 1 is described in Table 2 along with the average water content of the beads mixture and total water content in the liquid first part formulation. The total water content in the liquid first part is calculated by adding together the weight of all the sources of water in the liquid first part, i.e. the amount of water in the acrylic polymer dispersion and in the polymer beads 1 and 2. This is then expressed as a wt % of the overall liquid first part.

TABLE 2

|  | Composition | Average water content (wt %) of beads mixture | Total water content (wt %) in liquid first part |
|---|---|---|---|
| Example 3 | Polymer beads 1(b)/Polymer beads 2(b)/acrylic polymer dispersion: 21/49/30 wt % | 2.94 | 17.03 |
| Example 4 | Polymer beads 1(d)/Polymer beads 2(c)/acrylic polymer dispersion: 21/49/30 wt % | 5.158 | 18.58 |
| Example 5 | Polymer beads 1(f)/Polymer beads 2(c)/acrylic polymer dispersion: 21/49/30 wt % | 7.785 | 20.42 |
| Example 6 | Polymer beads 1(e)/Polymer beads 2(e)/acrylic polymer dispersion: 21/49/30 wt % | 12.7 | 23.86 |
| Comparative Example 1 | Polymer beads 1(a)/Polymer beads 2(a)/acrylic polymer dispersion: 24/56/20 wt % | 0.5 | 10.38 |

Shelf Life and Sedimentation Assessment of Liquid First Parts

The shelf life of the liquid first parts was assessed by carrying out an accelerated aging test. The general method is as follows: After preparing the liquid first parts, 30 gram aliquots of each liquid were poured into a series of clear sample vials fitted with screw-top lids and these were placed in an oven at 40° C. One sample vial of each liquid first part was removed periodically, cooled to 25° C. and checked for sedimentation. Sedimentation was assessed by slowly inverting the clear sample vial containing the liquid first part and a visual check made to assess for the presence of bead polymer sediment. For this particular system, the formulation was remixed prior to carrying out Brookfield viscosity determination. All samples were discarded after Brookfield viscosity determination. The Brookfield viscosity versus time was tabulated (Table 3)

TABLE 3

| | Brookfield viscosity (centipoise) | | | | |
|---|---|---|---|---|---|
| Days at 40° C. | Comparative Example 1 | Example 3 | Example 4 | Example 5 | Example 6 |
| 0 | 6,200 | 1,380 | 1,540 | 1,420 | 320 |
| 7 | 7,200 | 1,300 | 1,540 | 1,420 | 300 |
| 14 | 8,300 | 1,320 | 1,610 | 1,450 | 300 |
| 21 | >15,000 | 1,450 | 1,640 | 1,520 | 310 |
| 28 | solid | 1,400 | 1,650 | 1,510 | 300 |
| 42 | solid | 1,820 | 1,920 | 1,900 | 310 |

The results show that Comparative example 1 (not part of the invention) rapidly rises in Brookfield viscosity after 21 days, solidifying by 28 days and therefore has limited shelf life. On the other hand, Examples 3 to 6 display stable viscosity for at least 42 days storage at 40° C.

It can therefore be seen that when the total water content of the liquid first part is greater than approximately 10-11 wt %, the shelf life of the liquid first part and therefore, of the hardenable multi-part acrylic composition is increased.

It can therefore be seen that the liquid first part and thus the hardenable multi-part acrylic compositions according to the present invention have an increased shelf life than comparative example 1.

Example 7

Preparation of Hardenable Composition (Radiopacifying Filler in Liquid Second Part)

A liquid second part was prepared by firstly dissolving 12.0 g of poly(MMA-co-DMAEMA) copolymer in 47.52 g of MMA monomer (stabilised with 60 ppm hydroquinone (HQ) inhibitor) and 0.48 g of N,N-dimethyl-para-toluidine (DMPT) accelerator in a glass flask equipped with stirrer. The poly(MMA-co-DMAEMA) copolymer has comonomer ratio MMA:DMAEMA 95:5 wt %, was free of residual initiator and had reduced viscosity 0.50 dl/g. The required amount of barium sulphate (40.0 g) was then added with stirring at 500-600 rpm and left for 1 hour to disperse the barium sulphate in the monomer/polymer syrup. The Brookfield viscosity of the resultant liquid second part was 2,500 centipoise.

The preparation of a hardenable composition from the liquid first part of example 3 after ageing for 42 days at 40° C. and the above liquid second part was carried out as follows: Before mixing, the two components were equilibrated for at least 10 hours in an incubator at 23° C. 14.0 g of the liquid first part was placed into a polypropylene beaker followed by 14.0 g of the liquid second part. Hand mixing was then carried out at 23° C. for 30 seconds using a metal spatula, whereupon the material was covered and left to stand. The mixture increased in viscosity, undergoes polymerisation and hardens to a solid mass.

Comparative Example 2

Preparation of Hardenable Composition Using the Liquid First Part of Comparative Example 1.

A liquid second part containing radiopacifying filler was prepared according to example 7 and used in combination with the liquid first part of comparative example 1 after ageing for 42 days at 40° C. to make a hardenable composition, as follows:

Before mixing, the two components were equilibrated for at least 10 hours in an incubator at 23° C. 14.0 g of the liquid first part was placed into a polypropylene beaker followed by 14.0 g of the liquid second part. An attempt to carry out hand mixing of the two liquid parts was then carried out at 23° C. for 30 seconds using a metal spatula, but the solid nature of comparative example 1 after ageing for 42 days at 40° C. meant a homogeneous mixture was not produced and the polymerized mass that was formed was not uniform in consistency, therefore not considered to be a hardenable composition suitable for use as a medical implant material.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A hardenable multi-part acrylic composition including a storage stable liquid first part, a storage stable liquid second part and optionally, a third or further liquid parts, which react upon mixing to form a cement which hardens to a solid, the composition comprising an acrylic monomer component, an initiator component in an amount effective to polymerize the acrylic monomer component upon being mixed and/or activated therewith, wherein the liquid first part comprises an aqueous dispersion of acrylic polymer particles and acrylic polymer beads in the said dispersion, wherein the polymer beads in the dispersion are at an equilibrium water content with the aqueous phase of the dispersion.

2. The hardenable multi-part acrylic composition according to claim 1, wherein the monomer component and the initiator component are located in separate parts of the multi-part acrylic composition.

3. The hardenable multi-part acrylic composition according to claim 1, wherein the liquid second part comprises the acrylic monomer component.

4. The hardenable multi-part acrylic composition according to claim 1, wherein the equilibrium water content of the acrylic polymer beads when suspended in the aqueous dispersion is in the range 1.0-15% w/w with respect to the amount of acrylic polymer beads.

5. The hardenable multi-part acrylic composition according to claim 1, wherein the water content provided by the continuous phase of the aqueous dispersion at equilibrium is in the range 8-30% w/w liquid first part.

6. The hardenable multi-part acrylic composition according to claim 1, wherein the Brookfield viscosity range for the liquid first part and liquid second part is between 10 and 10,000 centipoise.

7. The hardenable multi-part acrylic composition according to claim 1, wherein the acrylic polymer beads are present in the hardenable acrylic composition at an amount between 15-80% w/w.

8. The hardenable multi-part acrylic composition according to claim 1, wherein the total water content of the liquid first part is in the range 16-45% w/w.

9. The hardenable multi-part acrylic composition according to claim 1, wherein the ratio of the acrylic polymer particles to the acrylic polymer beads is between 4:96 to 60:40 w/w.

10. The hardenable multi-part acrylic composition according to claim 1, wherein the acrylic polymer particles include one or more sub-population(s) of acrylic polymer particles.

11. The hardenable multi-part acrylic composition according to claim 1, wherein the acrylic polymer particles are emulsion polymerized acrylic polymer particles.

12. The hardenable multi-part acrylic composition according to claim 1, wherein the acrylic polymer beads include one or more sub-population(s) of acrylic polymer beads, wherein the mean particle size of a lower average particle size sub-population(s) is in the range 10-100 µm.

13. The hardenable multi-part acrylic composition according to claim 1, wherein the acrylic polymer particles in the aqueous dispersion together with the acrylic polymer beads form at least 90% of the polymer present in the liquid first part of the multi-part acrylic composition.

14. The hardenable multi-part acrylic composition according to claim 1, wherein at least 90% w/w of the total acrylic monomer component in the composition is present in the liquid second part.

15. The hardenable multi-part acrylic composition according to claim 1 wherein substantially all the acrylic monomer component in the composition is present in the liquid second part.

16. The hardenable multi-part acrylic composition according to claim 1, wherein the acrylic monomer component is present in only one part of the composition.

17. The hardenable multi-part acrylic composition according to claim 1, wherein the acrylic monomer component containing liquid part includes acrylic polymer dissolved therein.

18. The hardenable multi-part acrylic composition according to claim 1, wherein the amount of monomer in the unmixed composition, whether in the second part, or otherwise, is in the range 15-49.5% w/w.

19. The hardenable multi-part acrylic composition according to claim 1, wherein when both monomer and polymer form the bulk of the liquid second part, the ratio of acrylic monomer:polymer is in the range 98:2 to 50:50.

20. The hardenable multi-part acrylic composition according to claim 1, wherein at least 90% w/w of the total emulsion polymerized acrylic polymer particles present in the composition is present in the liquid first part.

21. The hardenable multi-part acrylic composition according to claim 1, wherein substantially all the emulsion polymerized acrylic polymer particles in the composition is present in the liquid first part.

22. The hardenable multi-part acrylic composition according to claim 1, wherein the emulsion polymerized acrylic polymer particles are present in only one part of the composition.

23. The hardenable multi-part acrylic composition according to claim 1, wherein at least 70 wt % of the total acrylic polymer bead is present in the liquid first part.

24. The hardenable multi-part acrylic composition according to claim 1, wherein all or substantially all of the said acrylic monomer component and the said emulsion polymerized acrylic polymer particles, if the latter is present, are located in separate parts of the said composition so that, the liquid carrier of the first part is provided by the dispersion liquid carrier and a liquid carrier for the second part is provided by the acrylic monomer.

25. The hardenable multi-part acrylic composition according to claim 1, wherein the ratio of the liquid first part to the liquid second part is in the range 1:5 to 5:1 by mass.

26. The hardenable multi-part acrylic composition according to claim 1, wherein the Z-average particle size of the acrylic polymer particles is less than 2000 nm.

27. The hardenable multi-part acrylic composition according to claim 1, wherein the weight average molecular weight (Mw) of the acrylic polymer particles is typically, between 25,000 daltons and 3,000,000 daltons.

28. The hardenable multi-part acrylic composition according to claim 1, wherein the average particle size of the acrylic polymer beads is in the range 10-1000 μm.

29. The hardenable multi-part acrylic composition according to claim 1, wherein the weight average molecular weight (Mw) of the acrylic polymer beads, is between 10,000 daltons and 3,000,000 daltons.

30. The hardenable multi-part acrylic composition according to claim 1, wherein a filler is present in the composition and the level of filler in the multi-part acrylic composition is up to 49.9% w/w of the multi-part acrylic composition.

31. The hardenable multi-part acrylic composition according to claim 30, wherein the fillers include radiopacifying fillers.

32. The hardenable multi-part acrylic composition according to claim 1, wherein radiopacifying fillers are selected from the list comprising zirconium dioxide, strontium carbonate, powdered tantalum, powdered tungsten, barium sulphate and mixtures thereof.

33. The hardenable multi-part acrylic composition according to claim 30, wherein the level of radiopacifying filler in the hardenable multi-part composition of the invention is between 1 and 50% w/w.

34. The hardenable multi-part acrylic composition according to claim 1, wherein a solid cement composition is produced from mixing a multi-part acrylic composition.

35. The hardenable multi-part acrylic composition according to claim 1, wherein an acrylic cement is produced.

36. The hardenable multi-part acrylic composition according to claim 1, further comprising a syringe or caulking gun or automated mixing device having at least two compartments comprising the liquid first part in a first compartment thereof and the liquid second part in the second compartment thereof.

37. The hardenable multi-part acrylic composition according to claim 1, wherein a multi-part bone cement or dental cement or building cement or structural adhesive or laminating adhesive or jointing or sealing composition according to any of claims 1 to 35.

38. The hardenable multi-part acrylic composition according to claim 1, wherein a medical implant material is produced from mixing a multi-part acrylic composition.

39. The hardenable multi-part acrylic composition according to claim 1, wherein the multi-part composition is used in surgery, or in the treatment of human or animal bone or teeth.

40. The hardenable multi-part acrylic composition according to claim 1, wherein the multi-part composition is used in the replacement or partial replacement of human or animal bone.

41. The hardenable multi-part acrylic composition according to claim 1, wherein the multi-part acrylic composition is used dentistry, in the treatment of human teeth or animal teeth, in veterinary surgery, or in the treatment of hoof, nail or horn.

42. The hardenable multi-part acrylic composition according to claim 1, wherein the multi-part composition is used in the replacement of partial replacement of human teeth or animal teeth, hoof, nail or horn.

43. The hardenable multi-part acrylic composition according to claim 1, wherein a solid cement composition is produced and wherein the solid cement composition is porous.

44. The hardenable multi-part acrylic composition according to claim 1, wherein according to claim 43, wherein the solid cement composition is a bone cement and wherein the porosity (size and topography) is adapted to provide controlled release of therapeutic agents into the surrounding bone and tissue.

45. The hardenable multi-part acrylic composition according to claim 1, comprising a pharmaceutically effective amount of a therapeutic agent.

46. The hardenable multi-part acrylic composition according to claim 1, wherein in a bone cement or dental cement composition the components thereof are biocompatible components at least once the composition is set to a solid.

* * * * *